United States Patent [19]

Hisada et al.

[11] 4,117,136
[45] Sep. 26, 1978

[54] SYSTEMIC ANTIMICROBIAL QUINOLINES FOR PLANT DISEASE

[75] Inventors: Yoshio Hisada, Kawanishi; Kiyoto Maeda, Takarazuka; Hideo Agui, Toyonaka, all of Japan

[73] Assignee: Sumitomo Chemical Company, Ltd., Osaka, Japan

[21] Appl. No.: 825,115

[22] Filed: Aug. 16, 1977

[30] Foreign Application Priority Data

Aug. 19, 1976 [JP] Japan .................................. 51-99322

[51] Int. Cl.² ............................................. A61K 31/47
[52] U.S. Cl. .................. 424/258; 260/283 S
[58] Field of Search ................. 260/287 AN; 424/258

[56] References Cited

U.S. PATENT DOCUMENTS

| 3,287,458 | 11/1966 | Kaminsky et al. | 260/287 AN |
|---|---|---|---|
| 3,524,858 | 8/1970 | Kaminsky et al. | 260/287 AN |
| 3,954,775 | 5/1976 | Agui et al. | 424/248 |

FOREIGN PATENT DOCUMENTS

| 832,343 | 12/1975 | Belgium. |
|---|---|---|
| 26,638 | 10/1974 | Japan. |
| 31,998 | 11/1972 | Japan. |
| 89,396 | 7/1975 | Japan. |
| 43,798 | 12/1974 | Japan. |
| 31,999 | 3/1971 | Japan. |

*Primary Examiner*—Donald G. Daus
*Assistant Examiner*—David E. Wheeler
*Attorney, Agent, or Firm*—Sughrue, Rothwell, Mion, Zinn and MacPeak; Sughrue, Rothwell, Mion, Zinn and Macpeak

[57] ABSTRACT

A method for preventing and eradicating bacterial infectious plant disease which comprises applying to plants a composition containing, as an active ingredient, at least one 4(1H)-oxo-3-quinolinecarboxylic acid derivative represented by the general formula (I):

wherein A represents —OCH$_2$O— (at the 6 and 7 position) or $$-S-\overset{O}{\underset{\underset{R_4}{|}}{C}}-N-$$

(at the 5 and 6 position), wherein $R_4$ represents a hydrogen atom or a lower alkyl group; $R_1$ represents a hydrogen atom, a lower alkyl group, an amino group, an ammonium group or an alkali metal atom; $R_2$ represents a lower alkyl group, a halogenated lower alkyl group, a hydroxyalkyl group, an alkenyl group, or an alkoxyl group; and $R_3$ represents a hydrogen atom or a lower alkyl group.

4 Claims, No Drawings

SYSTEMIC ANTIMICROBIAL QUINOLINES FOR PLANT DISEASE

BACKGROUND OF THE INVENTION

1. Field of the Invention

The present invention relates to a method for preventing and eradicating plant disease caused by bacterial infection and, more particularly, it relates to a plant disease prevention and eradication method which comprises applying a composition containing, as an effective component, a 4(1H)-oxo-3-quinolinecarboxylic acid derivative.

2. Description of the Prior Art

Recently, many new organic synthetic fungicides have been discovered as plant disease preventing agents and they have largely contributed to an increased production of foods. However, although they are effective for diseases caused by fungi, they are ineffective for bacterially caused diseases. Except for a few antibiotics (e.g., streptomycin, novobiocin, chloramphenicol, etc.) which have a narrow applicable range, chemical compositions exhibiting specific activities to bacterially caused plant diseases have not yet been developed.

SUMMARY OF THE INVENTION

On considering the importance of the prevention and eradication of bacterially caused diseases of agricultural and horticultural crops, various investigations have been made for the purpose of developing compositions for preventing bacterially caused plant diseases and, as the result thereof, it has now been discovered that the compounds represented by the general formula (I) below have a strong systemic activity in plants and a surprisingly excellent effect in the prevention and the eradication of these bacterially caused diseases of plants. Furthermore, it has also been found that the compounds of this invention do not adversely affect agricultural and horticultural crops.

Thus, according to the present invention, there is provided a method for preventing and eradicating plant diseases which comprises applying a composition containing, as an effective component, at least one 4(1H)-oxo-3-quinolinecarboxylic acid derivative represented by the general formula (I):

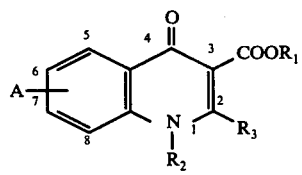

wherein A represents —OCH$_2$O—(attached to the 6 and 7 position) or

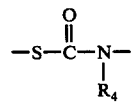

(attached to the 6 and 5 position), wherein R$_4$ represents a hydrogen atom or a (C$_1$-C$_4$)alkyl group; R$_1$ represents a hydrogen atom, a (C$_1$-C$_4$)alkyl group, an amino group, an ammonium group or an alkali metal atom; R$_2$ represents a (C$_1$-C$_4$)alkyl group, a halogenated (C$_1$-C$_4$)alkyl group, a (C$_1$-C$_4$)hydroxyalkyl group, a (C$_2$-C$_3$)alkenyl group, or a (C$_1$-C$_4$)alkoxyl group; and R$_3$ represents a hydrogen atom or a (C$_1$-C$_4$)alkyl group. In the above, the alkali metal atom preferably includes sodium and potassium atoms, and the halogenated (C$_1$-C$_4$)alkyl group preferably includes a (C$_1$-C$_4$)alkyl group substituted with a fluorine or chlorine atom.

DETAILED DESCRIPTION OF THE INVENTION

Some of the compounds of this invention within the scope of the general formula (I) are already known as antibacterial agents in the medical field as disclosed in, for example, U.S. Pat. No. 3,287,458, Japanese Patent Publication No. 26,638/74, and Japanese Patent Application (OPI) Nos. 31,998/72, 89,396/75 and 43,798/76, which describe the utilization of them as chemotherapeutic agents for animal diseases caused by bacteria. However, none of these references teach or suggest that these compounds could be utilized as agricultural and horticultural eradicants for plant diseases caused by bacterial infection.

As the result of intensive investigations on utilization of various medicines having chemotherapeutic properties as an agent for preventing and eradicating bacterially caused diseases of agricultural and horticultural crops, it has been discovered that only the compounds represented by the general formula (I) have quite excellent effects as such eradicants. Practically speaking, as shown in the test results of Table 2 in Example 1 given hereinafter, nalidixic acid and a sulfa drug such as sulfamine which are widely used for curing a urethral meatus infection and an intestinal infection as well as chlorhexidine which is used for the local prophylaxis of bacterial infections were all observed to have no effect for preventing the occurrence of the soft rot disease of Chinese cabbage caused by *Erwinia aroideae*, while the compounds of this invention showed an excellent effect superior to the comparison drug, streptomycin-sulfate.

Furthermore, by performing simultaneously an antibacterial test in vitro and a disease prevention test, a quite surprising result was obtained. It was found that Compounds Nos. 2, 8 and 11 in Example 2, which possess very weak antibacterial activity *Erwinia carotovora*, were observed to be highly effective in preventing and eradicating soft rot disease of Chinese cabbage caused by this bacterium. This fact shows clearly that chemotherapeutical materials used as medicaments cannot always be utilized as compositions for controlling plant diseases.

Moreover, as the result of further investigations of the properties of the compounds used in this invention, it has also been demonstrated that the compounds used in this invention have the property of readily being absorbed in a plant through the roots and translated into the aerial parts of the plant. This property contributes greatly to the antibacterial activity against bacteria which parasitize and propagate inside a plant. Accordingly, systemic action of antibacterial agents in a plant is essential for prevention and eradication of bacterial diseases. The reason that conventional antibacterial materials for medical use show almost no effect on plant disease control when they are practically applied to plants is due to lack of systemic activity in a plant. On the other hand, since the compounds of this invention have a high systemic activity in a plant, in addition to their antibacterial activity, the compounds exhibit quite high efficacy in preventing and eradicating bacterially caused plant diseases. These properties of the compounds only now have been discovered.

The compounds of this invention can be prepared by the processes described in the above-illustrated patent references and Japanese Patent Application (OPI) No. 31,999/72.

Some specific examples of the compounds which can be used in this invention are illustrated in Table 1 below but, as the matter of course, this invention is not to be construed as being limited to these compounds only.

TABLE 1

4(1H)-Oxo-3-quinolinecarboxylic Acid Derivatives

| Compound No. | Chemical Formula | Physical Property |
|---|---|---|
| (1) | [structure with N-$C_2H_5$, COOH] | m.p. 310° C (decomposition) |
| (2) | [structure with N-$C_2H_5$, $COOCH_3$] | m.p. 198–199° C |
| (3) | [structure with N-$OCH_3$, COOH] | m.p. 260° C (decomposition) |
| (4) | [structure with N-CH=$CH_2$, COOH] | m.p. 277–278° C |
| (5) | [structure with N-$CH_2CH_2OH$, COOH] | m.p. 303–305° C (decomposition) |
| (6) | [structure with N-$CH_2CF_3$, COOH] | m.p. 327–329° C |
| (7)* | [structure with N-$CH_2CH_2F$, COOH] | m.p. 311–314° C |
| (8)* | [structure with N-$CH_2CH_2F$, $COOC_2H_5$] | m.p. 229–230° C |

TABLE 1-continued
4(1H)-Oxo-3-quinolinecarboxylic Acid Derivatives

| Compound No. | Chemical Formula | Physical Property |
|---|---|---|
| (9)* | [structure: methylenedioxy-fused quinolinone with COOH at 3-position and N-CH$_2$CH$_2$Cl] | m.p. 279-280° C (decomposition) |
| (10) | [structure: quinolinone with 5-S(=O)-N(CH$_3$), COOH at 3-position, N-OCH$_3$] | m.p. 312-315° C (decomposition) |
| (11) | [structure: methylenedioxy-fused quinolinone with COOH at 3-position, 2-CH$_3$, N-C$_2$H$_5$] | m.p. 305° C (decomposition) |
| (12) | [structure: methylenedioxy-fused quinolinone with COONa at 3-position, N-C$_2$H$_5$] | m.p. more than 300° C (decomposition) |
| (13) | [structure: methylenedioxy-fused quinolinone with COONa at 3-position, N-CH=CH$_2$] | m.p. more than 300° C (decomposition) |

*Compounds 7,8 and 9 are compounds undisclosed in the prior art.

In the present invention, a method for eradicating plant disease caused by bacterial infection can be carried out by, for example, dusting, spraying or applying a compound of the formula (I) as described above to a plant, mingling it with soil around the plant roots or immersing a plant into a solution or suspension of a compound of the formula (I) so that a compound of the formula (I) comes in contact with the plant.

For this purpose, a compound of the formula (I) can be used alone, but usually it is used in the form of an appropriate agricultural preparation such as dusts, wettable powders, oilsprays, tablets, emusifiable concentrates, granules, fine granules, aerosols and the like.

These agricultural preparations can be prepared in a conventional manner by mixing a compound of the formula (I) with an appropriate solid or liquid carrier and appropriate adjuvants (e.g., surfactants, adherents, dispersants, stabilizers, etc.) for improving the dispersibility and other properties of the compound (I) at use.

Examples of appropriate solid carriers which can be used are a fine powder or granules of a botanical carrier (e.g., flour, tobacco stalk powder, soybean powder, walnut shell powder, wood powder, saw dust, bran, bark powder, cellulose powder, vegetable extract residue, etc.); fibrous materials (e.g., paper, corrugated cardboard and old rags, etc.); synthesized plastic powders; clays (e.g., kaolin, bentonite, fuller's earth, etc.); talcs; other inorganic minerals (e.g., pyrophyllite, sericite, pumice, sulfur powder, active carbon, etc.) and chemical fertilizers (e.g., ammonium sulfate, ammonium phosphate, ammonium nitrate, urea, ammonium chloride, etc.).

Examples of appropriate liquid carriers which can be used are water; alcohols (e.g., methyl alcohol, ethyl alcohol, etc.); ketones (e.g., acetone, methyl ethyl ketone, and the like); ethers (e.g., diethyl ether, dioxane, Cellosolve, tetrahydrofuran, etc.); aromatic hydrocarbons (e.g., benzene, toluene, xylene and methyl naphthalene, etc.); aliphatic hydrocarbons (e.g., gasoline, kerosene and lamp oil, etc.); esters; nitriles; acidamides (e.g., dimethylformamide, dimethylacetamide, etc.); and halogenated hydrocarbons (e.g., dichloroethane, carbon tetrachloride, etc.).

Examples of surfactants which can be used in the present invention are alkyl sulfuric ester alkyl sulfonates, alkylaryl sulfonate, polyethyleneglycol ethers and polyhydric alcohol esters. Examples of adherents and dispersants which can be used in the present invention may include casein, gelatin, starch powder, carboxymethyl cellulose, gum arabic, alginic acid, lignin, bentonite, molasses, polyvinyl alcohol, pine oil and agar. As a stabilizer, use can be made of members such as PAP (isopropyl acid phosphates mixture), TCP (tricresyl phosphate), tolu oil, epoxidized oil, various surfactants and various fatty acids and esters thereof.

Furthermore, if necessary, the compounds of this invention can be used as a mixture thereof with other agricultural chemicals such as fungicides, insecticides, miticides, nematocides, herbicides, plant growth regulators, synergists, etc., or fertilizers and, in this case, all of the components present can be effectively used without reducing the effect of any component.

The particular dosage of the compound (I) used in the present invention will be decided taking into consideration various conditions such as the kind, stage or degree of the disease to be eradicated, the properties of the compound, the growth circumstances of the plant and the like.

Generally speaking, a compound of the formula (I) may be used at a concentration of 10 to 2,000 ppm. For example, in case of field application, 10 to 300 g per 10 are of a compound of the formula (I) may be used at this concentration.

Diseases of agricultural and horticultural crops to which the compounds used in this invention are effective are described below in more detail. That is, the compounds used in this invention exhibit excellent disease prevention effects to many bacterially caused diseases of various crops such as bacterial leaf blight of rice, the soft rot of various vegetables, black rot, bacterial wilt of egg plants, the bacterial canker of tomatoes, angular leaf spot disease of melons, the bacterial canker of tulips, the shot hole of peaches, the wild fire of tobacco, the bacterial canker of citrus fruits, the fire blight of apples and pears, the black leg of potatoes, etc. Also, as is clear from the results shown in the examples described hereinafter, the compounds used in this invention exhibit excellent disease prevention effects not only when dusted or sprayed onto stalks and leaves but also when treated as a soil drench, by root immersion or as a seed dressing.

The invention will further be explained by reference to the following formulation embodiments and examples but the invention is not to be construed as being limited thereto. In addition, the numerical designations for the compounds used as the effective components in the formulation embodiments and the examples correspond to the numerical designations for the compounds shown hereinbefore in Table 1.

(a) Dust

By crushing and mixing well 2 parts by weight of Compound (1) and 98 parts by weight of clay, a powder containing 2% of active ingredient was obtained.

(b) Wettable Powder

By crushing and mixing well 20 parts by weight of Compound (4), 75 parts by weight of diatomaceous earth, and 5 parts by weight of a wetting extender (an alkylbenzenesulfonate), a wettable powder containing 20% of the active ingredient was obtained.

(c) Emulsifiable Concentrate

By mixing 10 parts by weight of Compound (9), 80 parts by weight of dimethyl sulfoxide, and 10 parts by weight of an emulsifying agent (a polyoxyethylene phenylphenol ether), an emulsifiable concentrate containing 10% of the active ingredient was obtained.

(d) Granules

By crushing and mixing well 5 parts by weight of Compound (7), 3.5 parts by weight of clay, and 1.5 parts by weight of a binder (polyvinyl alcohol) and, after kneading with water, granulating the mixture followed by drying, granules containing 5% of the active ingredient were obtained.

The following examples are given to illustrate the effects of the present invention more specifically. Unless otherwise indicated, all parts, percents, ratios and the like are by weight.

EXAMPLE 1

Test for Disease Prevention Effect on Soft Rot of Chinese Cabbage Caused by E. aroideae Onto Chinese cabbage (Brassica pekinesis Rupr. cr.) grown in a flower pot of a diameter of 9 cm at two-leaf stage, the test sample in a dilute emulsion form was sprayed at a rate of 7 ml per flower pot. Three days thereafter, the leaves of the Chinese cabbage were injured and inoculated with a suspension of E. aroideae. Thereafter, the flower pot was placed in a dark and moist chamber (90–100% RH) for 2 days at 28° C and then incidence of the disease was assessed in the following manner. That is, the severity of disease was calculated according to the following relationship by measuring the ratio of the diseased area of the leaves, classifying the severity into grades 0, 1, 2, . . . 8 depending on the degree of the disease and recording the number of leaves $n_0, n_1, n_2 \ldots n_5$ corresponding to the each disease index:

| Disease Index | Ratio of Diseased Area |
| --- | --- |
| 0 | No disease |
| 1 | Diseased area: less than 5% |
| 2 | " 5 to less than 30% |
| 4 | " 30 to less than 60% |
| 8 | " 60% or more |

$$\text{Disease Severity (\%)} = \frac{0 \times n_0 + 1 \times n_1 + \ldots + 8 \times n_5}{8 \times n} \times 100$$

Two flower pots with two plants in each were used for each treatment. The results obtained are shown in Table 2 below.

TABLE 2

Test Results of Disease Prevention Effect on Soft Rot of Chinese Cabbage

| Compound | Concentration of Active Ingredient (ppm) | Severity of Disease (%) |
| --- | --- | --- |
| (1) | 500 | 0 |
|  | 100 | 0 |
| (2) | 500 | 0 |
|  | 100 | 7 |

TABLE 2-continued
Test Results of Disease Prevention
Effect on Soft Rot of Chinese Cabbage

| Compound | Concentration of Active Ingredient (ppm) | Severity of Disease (%) |
|---|---|---|
| (3) | 500 | 0 |
|  | 100 | 9 |
| (4) | 500 | 0 |
|  | 100 | 0 |
| (5) | 500 | 0 |
|  | 100 | 14 |
| (6) | 500 | 0 |
|  | 100 | 0 |
| (7) | 500 | 0 |
|  | 100 | 0 |
| (8) | 500 | 0 |
|  | 100 | 0 |
| (9) | 500 | 0 |
|  | 100 | 0 |
| (10) | 500 | 0 |
|  | 100 | 12 |
| (11) | 500 | 0 |
|  | 100 | 4 |
| (12) | 500 | 0 |
|  | 100 | 0 |
| (13) | 500 | 0 |
|  | 100 | 0 |
| Nalidixic Acid * 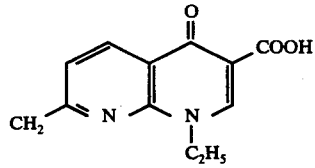 | 500 | 100 |
| Sulfamine * 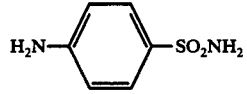 | 500 | 100 |
| Chlorohexidine * 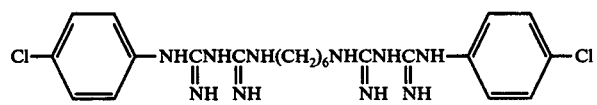 | 500 | 100 |
| Streptomycin Sulfate | 200 | 14 |
| Control (no spraying) | — | 100 |

\* Reference compounds which have chemotherapeutic activity against bacterial disease in warm-blooded animals, having antibacterial activities.

EXAMPLE 2

Simultaneous Test for Antibacterial Activity against *E. carotovora* and Curative Effect on Soft Rot of Chinese Cabbage Caused by *E. carotovora*

The test compound was mixed with a bacteriological culture medium containing 1.5% agar at various concentrations and the mixture was poured in a Petri dish of a diameter of 8 cm followed by solidifying. 24 hour-culture in a bacteriological culture medium of *E. carotovora* from a stock culture was diluted 10 times with sterilized water and inoculated on the agar culture medium. After incubation for 3 days at 27° C, the growth of the bacterium was observed, whereby the minimum inhibitory concentration (MIC, $\mu$g/ml) of each compound was determined. Evaluation test of curative effect on soft rot of Chinese cabbage caused by *E. carotovora* was carried out in a similar method to that of Example 1, except that samples were sprayed on a plant at a concentration of 500 ppm 16 hours after inoculation. The results obtained are shown in Table 3 below.

TABLE 3

| Test for Antibacterial Activity to Erwinia caratovara | | |
|---|---|---|
| Compound | MIC (μg/ml) | Severity of Disease |
| (1) | 1.56 | 0 |
| (2) | >50 | 12 |
| (3) | 0.39 | 0 |
| (4) | 0.78 | 0 |
| (6) | 3.12 | 0 |
| (7) | 0.78 | 0 |
| (8) | >50 | 8 |
| (9) | 1.56 | 0 |
| (10) | 0.049 | 0 |
| (11) | >50 | 12 |
| (12) | 1.56 | 0 |
| (13) | 0.78 | 0 |
| Nalidixic acid | 6.25 | 100 |
| Control (No spray) | — | 100 |

EXAMPLE 3

Plant Systemic Activity

Chinese cabbage (Nozaki #2) at the two-leaf stage grown in a flower pot of a diameter of 9 cm was withdrawn from the soil with care not to injure the roots and the roots of the Chinese cabbage were immersed in a solution of the test compound at a concentration of 10 ppm. After 2 days, a suspension of Erwinia carotovora was inoculated by scratching the leaves. The incidence of disease was assessed in the same manner as described in Example 1. Five plants were used for each treatment. The results obtained are shown in Table 4 below.

TABLE 4

| Plant Systemic Activity | | |
|---|---|---|
| Compound | Concentration of Active Ingredient (ppm) | Severity of Disease (%) |
| (1) | 10 | 0 |
| (2) | 10 | 0 |
| (4) | 10 | 0 |
| (7) | 10 | 0 |
| (8) | 10 | 0 |
| (9) | 10 | 0 |
| (10) | 10 | 25 |
| (13) | 10 | 0 |
| Streptomycin Sulfate* | 10 | 31 |
| None | — | 100 |

*Commercially available comparison compound containing streptomycin as the active ingredient.

EXAMPLE 4

Test for Disease Prevention Effect on Angular Leaf Spot of Cucumber

Onto a cucumber (*Cucumis sativus* L. Sagami Hanjiro Fushinari) at the two-leaf stage grown in a flower pot having a diameter of 9 cm the test sample in a water-soluble powder form was diluted with water and sprayed at a rate of 15 ml per pot. Four hours after the application of the sample, a suspension of *Pseudomonas lachrymans* was inoculated by spraying on the plant. Thereafter, the plant was placed in a moist chamber (90–100% RH) for 3 days at 25° C and then placed in a green house for 3–4 days. Incidence of disease was assessed in the following manner. That is, the severity of disease was calculated according to the following relationship by measuring the ratio of the diseased area of the leaves, classifying it into grades of 0, 0.5, 1, . . . 4, and recording the number of leaves $n_0, n_1, n_2 \ldots n_5$ corresponding to each index of the disease:

| Disease Index | Ratio of Diseased Area |
|---|---|
| 0 | Healthy |
| 0.5 | 1–3% disease spots |
| 1 | 1–10% diseased spot areas |
| 2 | 11–25% diseased spot areas |
| 3 | 26–50% diseased spot areas |
| 4 | >50% diseased spot areas |

$$\text{Diseased Severity} = \frac{0 \times n_0 + 0.5 \times n_1 + \ldots + 4 \times n_5}{4 \times n} \times 100$$

Five plants were used for each treatment. The results obtained are shown in Table 5 below.

TABLE 5

| Test for Disease Prevention Effect on Angular Leaf Spot of Cucumber | | |
|---|---|---|
| Compound | Concentration of Active Ingredient (ppm) | Severity of Disease (%) |
| (1) | 500 | 7.9 |
| (2) | 500 | 25 |
| (4) | 500 | 4.6 |
| (7) | 500 | 12 |
| (8) | 500 | 21 |
| (9) | 500 | 19 |
| (13) | 500 | 2.4 |
| Streptomycin Sulfate* | 200 | 28 |
| Kocide** | 830 | 46 |
| None | — | 80 |

*Commercially available comparison compound
**Commercially available comparison composition containing copper hydroxide as the active ingredient

EXAMPLE 5

Test for Disease Prevention Effect on Bacterial Wilt of Tomato

Tomatoes (breed: Sekai Ichi) at the 4–5 leaf stage grown in a flower pot of a diameter of 9 cm were inoculated with a soil drench of a suspension of *Pseudomonas solanacearum* at a rate of 20 ml per pot. After one day, the test compound in an emulsion form diluted with water was applied to the soil in the flower pot at a rate of 15 ml per pot. Then, after an additional 10 days, the incidence of disease condition was assessed. Four flower pots with two plants each were used for each treatment. The results obtained are shown in Table 6 below.

TABLE 6

| Test for Disease Prevention Effect on Bacterial Wilt of Tomato | | |
|---|---|---|
| Compound | Concentration of Active Ingredient (ppm) | Ratio of Diseased Seedling (%) |
| (1) | 500 | 10 |
| (2) | 500 | 36 |
| (4) | 500 | 6 |
| (7) | 500 | 18 |
| (8) | 500 | 24 |
| (9) | 500 | 14 |
| (13) | 500 | 4 |
| Streptomycin Sulfate* | 200 | 86 |
| None | — | 100 |
| None** | — | 0 |

*Commercially available comparison compound
**Neither treated nor inoculated

EXAMPLE 6

Test for Disease Prevention Effect on Bacterial Leaf Blight of Rice Plant

Onto a rice plant (breed: Kinki #33) at the 5-leaf stage grown in a flower pot of a diameter of 9 cm, the test sample in an emulsion form diluted with water was sprayed at a rate of 10 ml per pot. After 4 hours, a suspension of *Xanthomonas oryzae* was inoculated by scratching the central portion of the second leaf. The inoculated plant was placed in a moist chamber (90–100% RH) for 1 day and cultivated in a green house. Seven days after the inoculation, the incidence of disease was assessed using the bacterial-exudation method. That is, the bacteria exuded from the leaf section cut at portions 1, 3 and 5 cm apart from the inoculated portion of the plant were observed using a microscope and then the severity of disease was calculated by the following relationship.

$$\text{Disease Severity} = \frac{\text{Mean Bacterial Infected Distance}}{10} \times 100$$

Five flower pots with 10 plants each were used for each treatment. The results obtained are shown in Table 7 below.

TABLE 7
Test for Disease Prevention Effect on Bacterial Leaf Blight of Rice Plants

| Compound | Concentration of Active Ingredient (ppm) | Severity of Disease (%) |
| --- | --- | --- |
| (1) | 500 | 0 |
| (2) | 500 | 0 |
| (4) | 500 | 0 |
| (7) | 500 | 0 |
| (8) | 500 | 0 |
| (9) | 500 | 0 |
| (13) | 500 | 0 |
| Chloromycetin* | 200 | 1 |
| Phenazine** | 200 | 45 |

*Commercially available comparison composition containing chloroamphenicol as the active ingredient.
**Commercially available comparison composition containing phenazine-5-oxide as the active ingredient.

EXAMPLE 7

Test for Controlling Angular Leaf Spot of Cucumber by Seed Treatment

Seeds of cucumber (*Cucumis sativus* L. cv. Sagami Hanjiro Fushinari), which were inoculated by immersing them in a suspension of *P. lachrymans* at a concentration of $10^8$ to $10^9$ cells/ml for 30 minutes and followed by drying in air, were soaked in an aqueous solution of the test sample in an emulsion form for 30 minutes. Ten seeds were sowed in a flower pot containing sterilized soil. They were grown in a green house for 2 weeks. The number of infected cucumber plants were recorded. Fifty seeds were used for each treatment.

TABLE 8
Test for Controlling Angular Leaf Spot of Cucumber by Seed Treatment

| Compound | Concentration of Active Ingredient (ppm) | Infected Plants (%) |
| --- | --- | --- |
| (1) | 500 | 0 |
| (2) | 500 | 0 |
| (4) | 500 | 0 |
| (7) | 500 | 0 |
| (8) | 500 | 0 |
| (12) | 500 | 0 |
| (13) | 500 | 0 |
| Sodium Hypochlorite* | 2,000 | 7.5 |
| Streptomycin Sulfate* | 200 | 26.5 |
| Water | — | 77.3 |

*Commercially available comparison compound.

While the invention has been described in detail and with reference to specific embodiments thereof, it will be apparent to one skilled in the art that various changes and modifications can be made therein without departing from the spirit and scope thereof.

What is claimed is:

1. A method for eradicating and preventing bacterially caused plant diseases which comprises applying to plants by foliar spraying or soil drenching or to seeds by dressing or immersing, as an effective component, 4(1H)-oxo-3-quinoline-carboxylic acids represented by the formula (I):

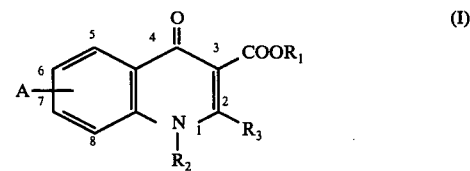

wherein A represents —OCH$_2$O—(attached at the 6- and 7-position) or

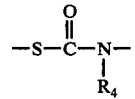

(attached at the 5- and 6-position), wherein R$_4$ represents a hydrogen atom or a (C$_1$–C$_4$)alkyl group; R$_1$ represents a hydrogen atom, a (C$_1$–C$_4$)alkyl group, an amino group, an ammonium group, or an alkali metal atom; R$_2$ represents a (C$_1$–C$_4$)alkyl group, a halogenated (C$_1$–C$_4$)alkyl group, a (C$_1$–C$_4$)hydroxyalkyl group, a (C$_2$–C$_3$)alkenyl group, or a (C$_1$–C$_4$)alkoxyl group; and R$_3$ represents a hydrogen atom or a (C$_1$–C$_4$)alkyl group.

2. The method according to claim 1, wherein A represents —OCH$_2$O— attached at the 6- and 7-position; R$_1$ represents a hydrogen atom, a sodium atom or a potassium atom; and R$_2$ represents a (C$_1$–C$_4$)alkyl group, a halogenated (C$_1$–C$_4$)-alkyl group or a (C$_2$–C$_3$)alkenyl group.

3. The method according to claim 1, wherein R$_2$ represents an ethyl group, a vinyl group or a monofluoroethyl group.

4. The method according to claim 1, wherein the active ingredient is a compound of the formula:

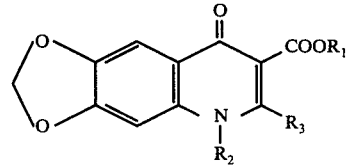

wherein R$_1$ represents a hydrogen atom, a sodium atom or a potassium atom; R$_3$ represents a hydrogen atom or a (C$_1$–C$_4$)-alkyl group; and R$_2$ represents an ethyl group, a vinyl group or a 2-fluoroethyl group.

* * * * *